United States Patent [19]

Möller et al.

[11] 4,112,109

[45] Sep. 5, 1978

[54] 4-SUBSTITUTED PYRAZOLES

[75] Inventors: Eike Möller, Wuppertal, Fed. Rep. of Germany; Karl Meng, deceased, late of Wuppertal, Fed. Rep. of Germany, by Ilse Heide Frieda Meng, legal representative; Egbert Wehinger, Neviges, Fed. Rep. of Germany; Harald Horstmann, Wuppertal, Fed. Rep. of Germany; Friedel Seuter, Neviges, Fed. Rep. of Germany

[73] Assignee: Bayer Aktiengesellschaft, Fed. Rep. of Germany

[21] Appl. No.: 766,187

[22] Filed: Feb. 7, 1977

Related U.S. Application Data

[62] Division of Ser. No. 693,970, Jun. 8, 1976.

[30] Foreign Application Priority Data

Jun. 13, 1975 [DE] Fed. Rep. of Germany ....... 2526467

[51] Int. Cl.² .......................................... A61K 31/415
[52] U.S. Cl. ................................................. 424/273 P
[58] Field of Search ..................................... 424/273 P

[56] References Cited

U.S. PATENT DOCUMENTS 4,002,641  1/1977  Moller et al. ...................... 424/273

Primary Examiner—Donald B. Moyer
Attorney, Agent, or Firm—Jacobs & Jacobs

[57] ABSTRACT

Pyrazoles of the formula

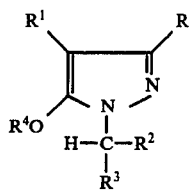

wherein
R is hydrogen, alkyl, aryl, aralkyl, trifluoromethyl or a heterocycle;
$R^1$ is aryl or aralkyl unsubstituted or substituted by halo, trifluoromethyl, alkyl, alkoxy or nitro; or a halo-substituted alkylthio moiety;
$R^2$ is lower alkyl; phenyl; or benzyl;
$R^3$ is aryl unsubstituted or substituted by alkyl, alkenyl, alkoxy, halo, trifluoromethyl, trifluoromethoxy, mono- or di-alkylamino, nitro, cyano, carboxamido, sulphonamido or $SO_n$-alkyl; phenyl having fused thereto a 5- to 7-membered isocyclic or heterocyclic ring, said heterocyclic ring having 1 or 2 oxygen or sulphur heteroatoms; or pyridyl; and
$R^4$ is unsubstituted or substituted carboacyl or sulphonyl;

are useful for their diuretic, saluretic, antihypertensive and antithrombotic properties.

22 Claims, No Drawings

4-SUBSTITUTED PYRAZOLES

CROSS-REFERENCE

This is a division of Ser. No. 693,970 filed June 8, 1976.

The present invention is concerned with pyrazoles, processes for their production, pharmaceutical compositions wherein said compounds are the active agents and to methods of effecting diuresis and saluresis in humans and animals, treating hypertension in humans and animals and treating thromboses in humans and animals utilizing said compounds.

It is known that pyrazole derivatives are useful as antipyretics, analgesics and antiphlogistics (see G. Erhart and H. Ruschig, *Arzneimittel* [Medicaments], Volume 1, page 148 (1972)).

In U.S. Ser. Nos. 521,906; 638,517; 637,861; 515,448, now U.S. Pat. No. 3,950,528; 459,467, now U.S. Pat. No. 3,949,083; 610,150, now U.S. Pat. No. 4,032,646; 549,408, now U.S. Pat. No. 4,018,890; 633,601, now U.S. Pat. No. 4,045,571; 633,636; 461,285, now U.S. Pat. No. 3,952,008; 543,664; 578,516, now U.S. Pat. No. 3,992,404; 631,946, now U.S. Pat. No. 4,056,533; 632,165, now U.S. Pat. No. 4,000,294; 619,891; and 582,773, now U.S. Pat. No. 5,053,621; pyrazolones and pyrazoles are disclosed which are useful for their diuretic, saluretic and antihypertensive properties. The compounds of the present invention differ structurally from the compounds of said applications; in particular, by the nature of the 5-position substituent, and, in part, by the nature of the group which links the 1-position ring nitrogen with the substituent at the 1-position.

More particularly, the present invention is concerned with pyrazoles of the formula

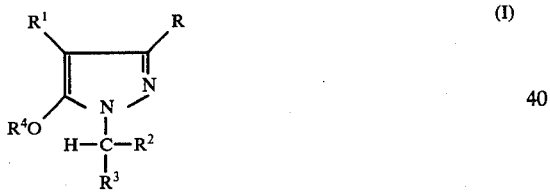

(I)

wherein

R is hydrogen, alkyl, especially lower alkyl, trifluoromethyl, aryl especially of 6 to 10 carbon atoms, aralkyl especially of 6 to 10 carbon atoms in the aryl moiety and 1 to 4 carbon atoms in the alkyl moiety particularly benzyl, or a heterocycle preferably of 5 to 7 members;

$R^1$ is aryl preferably of 6 to 10 carbon atoms unsubstituted or substituted by 1 to 3 of the same or different substituents selected from the group consisting of alkyl alkenyl preferably lower alkyl and especially of 1 to 4 carbon atoms, alkoxy especially lower alkoxy and preferably of 1 to 4 carbon atoms, halo especially fluoro, chloro and bromo, trifluoromethyl, trifluoromethoxy, cyano and nitro; aralkyl especially of 6 to 10 carbon atoms in the aryl moiety and 1 to 4 carbon atoms in the alkyl moiety unsubstituted or substituted by 1 to 3 of the same or different substituents selected from the group consisting of alkyl preferably lower alkyl, alkenyl and especially of 1 to 4 carbon atoms, alkoxy especially lower alkoxy and preferably of 1 to 4 carbon atoms, halo especially fluoro, chloro and bromo, trifluoromethyl and nitro; or haloalkylthio especially of 1 to 4 carbon atoms in the alkyl moiety and 1 to 3 halo atoms;

$R^2$ is lower alkyl; phenyl; or benzyl;

$R^3$ is aryl especially of 6 to 10 carbon atoms unsubstituted or substituted by 1 to 3 of the same or different substituents selected from the group consisting of alkyl especially lower alkyl and preferably of 1 to 4 carbon atoms, alkenyl especially lower alkenyl and preferably of 2 to 4 carbon atoms, alkoxy especially lower alkoxy and preferably of 1 to 4 carbon atoms, halo especially fluoro, chloro and bromo, trifluoromethyl, trifluoromethoxy, mono- or dialkylamino especially lower alkylamino and preferably of 1 to 4 carbon atoms in the alkyl moiety, nitro, cyano, carboxamido, sulphonamido and $SO_n$-alkyl wherein $n$ is 0 to 2; phenyl having fused thereto a 5- to 7-membered isocyclic or heterocyclic ring, said heterocyclic ring having 1 or 2 oxygen or sulphur heteroatoms; or pyridyl; and $R^4$ is a substituted carboacyl or sulphonyl moiety especially of the formula $R^5CO$ wherein $R^5$ is lower alkyl; lower alkoxy; haloalkyl of 1 to 4 carbon atoms in the alkyl moiety and 1 to 3 halo atoms; cycloalkyl of 5 to 7 carbon atoms; lower alkylthio; haloalkoxy of 1 to 4 carbon atoms in the alkoxy moiety and 1 to 3 halo atoms; haloalkylthio of 1 to 4 carbon atoms in the alkyl moiety and 1 to 3 halo atoms; lower alkoxy(lower alkyl); mono- or di-lower alkylamino(lower alkyl); phenyl unsubstituted or substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, $SO_n$-alkyl of 1 to 4 carbon atoms in the alkyl moiety and $n$ is 0 to 2, $SO_n$—$CF_3$ wherein $n$ is 0 to 2, carbonamido and sulphonamido; phenyl having fused thereto a 5- to 7-membered heterocyclic ring having 1 or 2 oxygen or sulphur atoms; or a 5- to 7-membered heterocyclic ring unsubstituted or substituted by alkyl of 1 to 4 carbon atoms, halo or nitro; or $R^6SO_2$ wherein $R^6$ is lower alkyl; cycloalkyl of 5 to 7 carbon atoms; or phenyl substituted by 1 or 2 substituents selected from the group consisting of alkyl of 1 to 4 carbon atoms, halo, trifluoromethyl, trifluoromethoxy, nitro, cyano and trifluoromethylsulphonyl.

The compounds of formula (I) contain an asymmetric carbon atom and the racemates can, of course, be resolved into the optical antipodes. Either the racemates or the antipodes or their salts can be administered as the active agent.

The pyrazoles of formula (I) of the present invention are produced when 5-pyrazolone derivatives of the formula

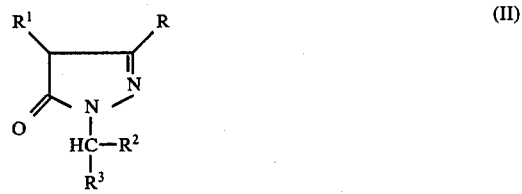

(II)

wherein R, $R^1$, $R^2$ and $R^3$ are as above defined, are reacted with acid derivatives, preferably with carboxylic acid or carbonic acid derivatives which contain the appropriate unsubstituted or substituted carboacyl moiety or with a sulphonic acid derivative which contains the appropriate substituted or unsubstituted sulphonyl moiety. These may be represented by the formula

(III)

wherein

X is a moiety which is eliminated under the conditions of the reaction, such as halo, a 5-membered heterocyclic azole ring, an alkyl moiety which is bonded to the carbonyl carbon atom via an oxygen or sulphur atom or a phenyl moiety unsubstituted or substituted by 1 or 2 nitro moieties or an acyloxy moiety; and Y is $R^5$ wherein $R^5$ is as above defined; or by the formula $$Z-SO_2-X' \qquad (IV)$$

wherein X' is halo; and Z is $R^6$ wherein $R^6$ is as above defined;

either in the presence or absence of inert organic solvents and basic materials such as alkali metal hydroxides and carbonates or alkaline earth metal hydroxides and carbonates or organic bases such as triethylamine or pyridine, at a temperature of from about −20° C. to +150° C.

The optical antipodes of the compounds according to the present invention are prepared in accordance with methods known from the literature (compare, for example, Houben-Weyl, IV/2, pages 509 et seq.) by interaction of the compound according to the present invention with a chiral medium such as, for example, by recrystallization from an optically active solvent or by chromatography on a chiral carrier substance or by reaction of the optically pure 5-pyrazolone derivatives of the formula (II) with the appropriate carboxylic acid derivatives, carbonic acid derivatives or sulphonic acid derivatives of the formulae (III) and (IV).

According to one embodiment of the present invention

R is hydrogen, lower alkyl, trifluoromethyl, aryl of 6 to 10 carbon atoms, aralkyl of 6 to 10 carbon atoms in the aryl moiety and 1 or 2 carbon atoms in the alkyl moiety, or a 5- to 7-membered heterocyclic moiety;

$R^1$ is a haloalkylthio of 1 to 4 carbon atoms in the alkyl moiety and 1 to 3 halo atoms; aryl of 6 to 10 carbon atoms unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, halo, trifluoromethyl, trifluoromethoxy, nitro and cyano; or aralkyl of 6 to 10 carbon atoms in the aryl moiety and 1 or 2 carbon atoms in the alkyl moiety unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, halo, trifluoromethyl, trifluoromethoxy, nitro and cyano;

$R^2$ is lower alkyl, phenyl or benzyl;

$R^3$ is aryl of 6 to 10 carbon atoms unsubstituted or substituted by 1 to 3 of the same or different substituents selected from the group consisting of alkyl of 1 to 4 carbon atoms, alkenyl of 2 to 4 carbon atoms, alkoxy of 1 to 4 carbon atoms, halo, trifluoromethyl, trifluoromethoxy, mono- or di-alkylamino of 1 to 4 carbon atoms in each alkyl moiety, nitro, cyano, carboxamido, sulphonamido and $SO_n$-alkyl of 1 to 4 carbon atoms in the alkyl moiety and wherein n is 0 to 2; phenyl having fused thereto a 5- to 7-membered isocyclic or heterocyclic ring, said heterocyclic ring having 1 or 2 oxygen or sulphur heteroatoms; or pyridyl; and $R^4$ is $R^5CO$ wherein $R^5$ is lower alkyl, cycloalkyl of 5 to 7 carbon atoms, halo(lower alkyl), lower alkoxy, lower alkylthio, halo(lower alkoxy), halo(lower alkylthio), lower alkoxy(lower alkyl), mono- or di(lower alkylamino), phenyl substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, carboxamido, sulphonamido, $SO_n$-(lower alkyl) wherein n is 0 to 2, and $SO_n-CF_3$ wherein n is 0 to 2; phenyl having fused thereto a 5- to 7-membered isocyclic or heterocyclic ring, said heterocyclic ring having 1 or 2 oxygen or sulphur heteroatoms; or a 5- to 7-membered heterocyclic ring unsubstituted or substituted by alkyl of 1 to 4 carbon atoms, halo or nitro; or $R^4$ is $R^6SO_2$ wherein $R^6$ is lower alkyl, cycloalkyl of 5 to 7 carbon atoms or phenyl substituted by 1 or 2 substituents selected from the group consisting of alkyl of 1 to 4 carbon atoms, halo, trifluoromethyl, trifluoromethoxy, nitro and $CF_3SO_2$.

According to another embodiment of the present invention

R is alkyl of 1 to 4 carbon atoms, trifluoromethyl, aryl of 6 to 10 carbon atoms, aralkyl of 6 to 10 carbon atoms in the aryl moiety and 1 or 2 carbon atoms in the alkyl moiety, or a 5- to 7-membered heterocyclic moiety;

$R^1$ is haloalkylthio; aryl of 6 to 10 carbon atoms unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy, nitro and cyano; or aralkyl of 6 to 10 carbon atoms in the aryl moiety and 1 or 2 carbon atoms in the alkyl moiety unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy, nitro and cyano;

$R^2$ is alkyl of 1 to 4 carbon atoms; phenyl or benzyl;

$R^3$ is aryl of 6 to 10 carbon atoms unsubstituted or substituted by 1 to 3 of the same or different substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy, mono- or di-alkylamino of 1 to 4 carbon atoms in each alkyl moiety, nitro, cyano, carboxamido, sulphonamido and $SO_n$-alkyl of 1 to 4 carbon atoms in the alkyl moiety and wherein n is 0 to 2; phenyl having fused thereto a 5- to 7-membered isocyclic or heterocyclic ring, said heterocyclic ring having 1 or 2 oxygen or sulphur heteroatoms; or pyridyl; and $R^4$ is $R^5CO$ wherein $R^5$ is alkyl of 1 to 4 carbon atoms, cycloalkyl of 5 to 7 carbon atoms, haloalkyl of 1 to 4 carbon atoms in the alkyl moiety, lower alkoxy, alkylthio of 1 to 4 carbon atoms in the alkyl moiety, haloalkylthio of 1 to 4 carbon atoms in the alkyl moiety, alkoxyalkyl of 1 to 4 carbon atoms in the alkoxy and in the alkyl moieties, mono- or dialkylamino of 1 to 4 carbon atoms in the alkyl moiety, phenyl substituted by 1 to 3 substituents selected from the group consisting of alkyl of 1 to 4 carbon atoms, alkoxy of 1 to 4 carbon atoms, fluoro, chloro, bromo, trifluoromethyl, trifluoromethoxy, nitro, cyano, carboxamido, sulphonamido, $SO_n$-alkyl of 1 to 4 carbon atoms in the alkyl moiety wherein $n$ is 0 to 2, and $SO_n$—$CF_3$ wherein $n$ is 0 to 2; phenyl having fused thereto a 5- to 7-membered isocyclic or heterocyclic ring, said heterocyclic ring having 1 or 2 oxygen or sulphur heteroatoms; or a 5- to 7-membered heterocyclic ring unsubstituted or substituted by alkyl of 1 to 4 carbon atoms, fluoro, chloro, bromo or nitro; or $R^4$ is $R^6SO_2$ wherein $R^6$ is alkyl of 1 to 4 carbon atoms, cycloalkyl of 5 to 7 carbon atoms or phenyl substituted by 1 or 2 substituents selected from the group consisting of alkyl of 1 to 4 carbon atoms, fluoro, chloro, bromo, trifluoromethyl, trifluoromethoxy, nitro and $CF_3SO_2$.

According to another embodiment of the present invention

R is hydrogen, alkyl of 1 to 4 carbon atoms, trifluoromethyl, phenyl or benzyl;

$R^1$ is chloroalkylthio of 1 to 4 carbon atoms in the alkyl moiety and 1 to 3 chloro atoms; phenyl unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy, nitro and cyano; or benzyl unsubstituted or substituted by 1 or 2 of the same or different substituents selected from the group consisting of alkyl of 1 to 4 carbon atoms, alkenyl of 2 to 4 carbon atoms, alkoxy of 1 to 4 carbon atoms, fluoro, chloro, bromo, trifluoromethyl, trifluoromethoxy, nitro and cyano;

$R^2$ is alkyl of 1 to 4 carbon atoms;

$R^3$ is phenyl substituted by 1 or 2 of the same or different substituents selected from the group consisting of alkyl of 1 to 8 carbon atoms, alkenyl of 2 to 8 carbon atoms, alkoxy of 1 to 6 carbon atoms, cycloalkyl of 5 to 7 carbon atoms, cycloalkenyl of 5 to 7 carbon atoms, fluoro, chloro, bromo, trifluoromethyl, trifluoromethoxy, nitro, cyano, dialkylamino of 1 to 4 carbon atoms in each alkyl moiety, carboxamido, sulphonamido or carboxamido or sulphonamido wherein 1 or both of the hydrogen atoms are substituted by 1 or 2 alkyl moieties of 1 to 4 carbon atoms, or wherein said alkyl moieties together with the nitrogen atom to which they are attached form a 5- to 7-membered heterocyclic ring, said ring containing nitrogen as the only heteroatom or said ring also containing oxygen as a heteroatom, and $SO_n$-alkyl of 1 to 4 carbon atoms in the alkyl moiety wherein $n$ is 0 or 2; phenyl having fused thereto a saturated or unsaturated 5- to 7-membered isocyclic or heterocyclic ring, said heterocyclic ring having an oxygen or sulphur heteroatom; naphthyl; or pyridyl.

According to another embodiment of the present invention $R^3$ is phenyl substituted by 1 or 2 of the same or different substituents selected from the group consisting of methyl, chloro, fluoro or trifluoromethyl; or tetramethylenephenyl.

According to another embodiment of the present invention $R^4$ is alkylcarbonyl of 1 to 6 carbon atoms in the alkyl moiety; alkoxycarbonyl of 1 to 6 carbon atoms in the alkoxy moiety; haloalkylcarbonyl of 1 to 6 carbon atoms in the alkyl moiety and 1 to 3 halo atoms; alkoxyalkylcarbonyl of 1 to 6 carbon atoms in the alkoxy and alkyl moieties; benzoyl nuclear substituted by 1 or 2 substituents selected from the group consisting of alkyl of 1 to 4 carbon atoms, halo, trifluoromethyl, trifluoromethoxy and nitro, or by 1 trifluoromethylsulphonyl; dialkylaminoalkylcarbonyl of 1 to 4 carbon atoms in each of the alkyl moieties; pyrrylcarbonyl; thienylcarbonyl; halothienylcarbonyl; furylcarbonyl; halofurylcarbonyl; pyrazolylcarbonyl; alkylpyrazolylcarbonyl of 1 to 4 carbon atoms in the alkyl moiety; imidazolylcarbonyl; alkylimidazolylcarbonyl of 1 to 4 carbon atoms in the alkyl moiety; thiazolylcarbonyl; nitrothiazolylcarbonyl; oxyzolylcarbonyl; isoxazolylcarbonyl; alkylisoxazolylcarbonyl of 1 to 4 carbon atoms in the alkyl moiety; halopicolinylcarbonyl; nicotinylcarbonyl; halonicotinylcarbonyl; pyridazinylcarbonyl; pyrimidinylcarbonyl; pyrazinylcarbonyl; alkylpiperazinylcarbonyl of 1 to 4 carbon atoms in the alkyl moiety; dihydrofurylcarbonyl; tetrahydrofurylcarbonyl; tetrahydropyridylcarbonyl; alkylpiperadylcarbonyl of 1 to 4 carbon atoms in the alkyl moiety; tetrahydropyranylcarbonyl; tetrahydrothiopyranylcarbonyl; thiadiazolylcarbonyl; morpholinocarbonyl; or phenylsulphonyl substituted by 1 or 2 substituents selected from the group consisting of alkyl of 1 to 4 carbon atoms, halo and nitro, or by 1 trifluoromethylsulphonyl moiety.

According to another embodiment of the present invention

R is hydrogen, alkyl of 1 to 3 carbon atoms, trifluoromethyl or benzyl;

$R^1$ is phenyl unsubstituted or substituted by alkyl of 1 to 3 carbon atoms, alkoxy of 1 to 3 carbon atoms, trifluoromethyl, trifluoromethoxy, halo, methyl, thio, nitro or cyano;

$R^2$ is methyl or ethyl;

$R^3$ is phenyl substituted by 2 halo atoms; or tetramethylenephenyl; and $R^4$ is acetyl; benzoyl nuclear substituted by 1 or 2 substituents selected from the group consisting of alkyl of 1 or 2 carbon atoms, alkoxy of 1 or 2 carbon atoms, fluoro, chloro, trifluoromethyl, nitro and cyano; or furylcarbonyl;

According to another embodiment of the present invention $R^4$ is acetyl; benzoyl nuclear substituted by 1 or 2 substituents selected from the group consisting of methyl, methoxy, fluoro, chloro, trifluoromethyl, nitro and cyano; or furylcarbonyl.

According to another embodiment of the present invention

R is alkyl of 1 to 3 carbon atoms, trifluoromethyl, or phenyl;

R[1] is phenyl substituted by alkyl of 1 or 2 carbon atoms, alkoxy of 1 or 2 carbon atoms, chloro or fluoro; or benzyl;

R[2] is methyl or ethyl;

R[3] is phenyl substituted by 1 or 2 of the same or different substituents selected from the group consisting of alkyl of 1 or 2 carbon atoms, chloro, fluoro and trifluoromethyl; naphthyl; tetramethylenephenyl; or pyridyl; and R[4] is R[5]CO wherein R[5] is alkyl of 1 to 4 carbon atoms, haloalkyl of 1 to 4 carbon atoms in the alkyl moiety and 1 to 3 halo atoms selected from the group consisting of chloro and fluoro; alkoxy of 1 to 4 carbon atoms; mono- or di-alkylamino of 1 to 4 carbon atoms in the each alkyl moiety; phenyl substituted by 1 to 3 substituents selected from the group consisting of alkyl of 1 or 4 carbon atoms, alkoxy of 1 or 4 carbon atoms, fluoro, chloro and trifluoromethylsulphonyl; or a 5- to 7-membered heterocyclic ring unsubstituted or substituted by alkyl of 1 or 4 carbon atoms, fluoro, chloro or nitro; or R[4] is R[6]SO[2] wherein R[6] is phenyl substituted by 1 or 2 substituents selected from the group consisting of alkyl of 1 or 4 carbon atoms, chloro, fluoro, nitro and trifluoromethylsulphonyl.

According to another embodiment of the present invention

R[4] is R[5]CO wherein R[5] is alkyl of 1 or 2 carbon atoms, haloalkyl of 1 or 2 carbon atoms in the alkyl moiety and 1 to 3 halo atoms selected from the group consisting of chloro and fluoro; alkoxy of 1 or 2 carbon atoms; mono- or di-alkylamino of 1 or 2 carbon atoms in each alkyl moiety; phenyl substituted by 1 to 3 substituents selected from the group consisting of alkyl of 1 or 2 carbon atoms, alkoxy of 1 or 2 carbon atoms, fluoro, chloro and trifluoromethylsulphonyl; or a 5- to 7-membered heterocyclic ring unsubstituted or substituted by alkyl of 1 or 2 carbon atoms, fluoro, chloro or nitro.

According to another embodiment of the present invention

R is alkyl of 1 or 2 carbon atoms or pyridyl;

R[1] is phenyl;

R[2] is methyl;

R[3] dichlorophenyl or tetramethylenephenyl; and

R[4] acetyl, methylbenzoyl, methoxybenzoyl, chlorobenzoyl, fluorobenzoyl, dichlorobenzoyl or furylcarbonyl.

Depending on the nature of the starting materials used, the synthesis of the compounds according to the present invention can be represented by the following equation in which 3-methyl-4-phenyl-1-(α-methyl-4-chlorobenzyl)-5-pyrazolone and acetyl chloride have been chosen as examples:

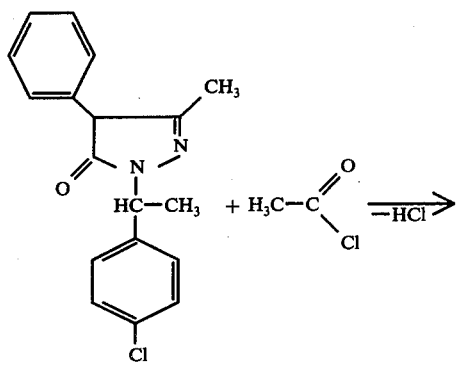

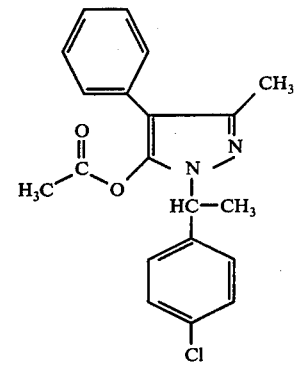

The 5-pyrazolone derivatives of formula (II), used as starting materials, have not been previously disclosed but can be prepared in accordance with methods known from the literature (compare, for example, L. Knorr, Ber. dtsch. Chem. Ges. 16, 2,597 (1883)), by reacting hydrazines of the formula (V) with β-carbonyl-fatty acid derivatives of the formula

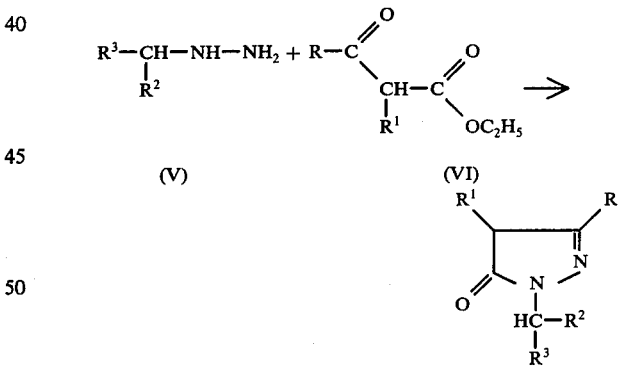

wherein R, R[1], R[2] and R[3] are as above defined,

The following compounds are representative of the 5-pyrazolones of formula (II): 3-methyl-4-phenyl-1-(α-methyl-3-fluorobenzyl)-5-pyrazolone, 3-methy-4-phenyl-1-(α-methyl-4-fluorobenzyl)-5-pyrazolone, 3-methyl-4-phenyl-1-(α-methyl-3-chlorobenzyl)-5-pyrazolone, 3-methyl-4-phenyl-1-(α-methyl-4-chlorobenzyl)-5-pyrazolone, 3-ethyl-4-phenyl-1-(α-methyl-4-bromobenzyl)-5-pyrazolone, 3-methyl-4-phenyl-1-(α-methyl-3,4-dichlorobenzyl)-5-pyrazolone, 4-(4-chlorophenyl)-1-(α-methyl-3,4-dichlorobenzyl)-5-pyrazolone, 4-(4-methylphenyl)-1-(α-methyl-3,4-dichlorobenzyl)-5-pyrazolone, 4-(3,4-dichlorophenyl)-1-(α-methyl-3,4-dichlorobenzyl)-5-pyrazolone, 3-methyl-4-phenyl-1-(α-methyl-3- chloro-4-methylbenzyl)-5-pyrazolone, 3-phenyl-4-phenyl-1-(α-methyl-3,4-dichlorobenzyl)-5-pyrazolone, 3-phenyl-4-phenyl-1-(α-methyl-3-chloro-4-methylbenzyl)-5-pyrazolone, 3-phenyl-4-phenyl-1-(α-(naphthyl-(2))-ethyl)-5-pyrazolone and 3-phenyl-4-phenyl-1-(α-methyl-3,4-tetramethylenebenzyl)-5-pyrazolone.

In formula (III)

 (III)

Y is preferably $R^5$ according to the embodiments set forth above.

X is preferably is halo, such as fluoro, chloro or bromo, especially chloro, or a 5-membered heterocyclic azole ring, such as imidazole, pyrazole, 1,3,4-triazole, especially imidazole, wherein the heterocyclic ring is bonded to the carbonyl carbon atom in formula (III) via a nitrogen, or is $R^7$ which is bonded to the carbonyl atom in formula (III) via an oxygen atom or a sulphur atom and which is a straight or branched chain alkyl moiety of 1 to 4 carbon atoms, phenyl unsubstituted or substituted by 1 or 2 nitro moieties or an acyloxy moiety of the formula

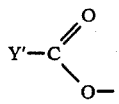

wherein Y' has the same meaning as Y but need not be idential to Y so that mixed anhydrides may also be employed.

The starting materials used in accordance with formula (III) are known from the literature and can be prepared according to methods known from the literature (compare, for example, Houben Weyl, *Methoden der organischen Chemie* (Methods of Organic Chemistry), VIII, page 101 (1952), Weygand/Hilgetag, *Org. Chemische Experimentierkunst* (The Art of Experimentation in Organic Chemistry), page 246, 4th edition, 1970, Verlag J. A. Barth, Leipzig).

The following starting materials are representative of those which may be used according to the present invention: acetyl chloride, propionyl chloride, isopropionyl chloride, acetic anhydride, trifluoroacetic anhydride, propionic anhydride, butyric anhydride, β-methoxy-propionic acid chloride, phenylacetic acid chloride, phenoxyacetic acid chloride, 4-chlorophenoxyacetic acid chloride, ethoxycarbonyl acetate, phenoxycarbonyl acetate, benzoyl chloride, benzoic anhydride, thiobenzoic acid S-phenyl ester, ethoxycarbonyl benzoate, $N^1$-benzoylimidazolide, 4-chlorobenzoyl chloride, 4-fluorobenzoyl chloride, 4-trifluoromethylbenzoyl chloride, 4-trifluoromethylsulphonylbenzoyl chloride, 4-trifluoromethoxybenzoyl chloride, (4-trifluoromethylthio)-benzoyl chloride, 3,4-dichlorobenzoyl chloride, 3-chloro-4-methylbenzoyl chloride, 4-nitrobenzoyl chloride, 4-methoxybenzoyl chloride, chlorocarbonic acid ethyl ester, chlorocarbonic acid isobutyl ester, chlorocarbonic acid benzyl ester, chlorocarbonic acid β-methoxyethyl ester, chlorocarbonic acid β-phenoxyethyl ester, carbonic acid diethyl ester, carbonic acid di-n-butyl ester, pyrocarbonic acid diethyl ester, N,N-dimethylcarbamic acid chloride, N,N-diethylcarbamic acid chloride, N,N-di-n-butylcarbamic acid chloride, pyridine-2-carboxylic acid chloride, nicotinic acid chloride, isonicotinic acid chloride, thiophene-2-carboxylic acid chloride, thiophene-3-carboxylic acid chloride, furane-2-carboxylic acid chloride, furane-3-carboxylic acid chloride, pyrazole-4-carboxylic acid 4-nitrophenyl ester, the anhydride of pyrazole-3-carboxylic acid and carbonic acid monoethyl ester,4-methyl-imidazole-5-carboxylic acid chloride, $N^1$-methyl-imidazole-4-carboxylic acid chloride, isoxazole-3-carboxylic acid chloride, 5-methyl-isoxazole-3-carboxylic acid chloride, isoxazole-4-carboxylic acid chloride, 5-methyl-isoxazole-4-carboxylic acid chloride, isoxazole-5-carboxylic acid chloride, 3-methylisoxazole-5-carboxylic acid chloride, isothiazole-3-carboxylic acid chloride, N-methylpyrrolidine-4-carboxylic acid chloride, ethoxycarbonyl-pyrrolidine-2-carboxylate, N-chlorocarbonyl-piperidine, N-methyl-N'-chlorocarbonylpiperazine and N-chlorocarbonyl-morpholine.

In formula (IV)

$$Z-SO_2-X' \qquad (IV)$$

Z is $R^6$ according to the embodiments set forth above and X' is halo, especially chlorine.

The starting materials used according to formula (IV) are known from the literature or can be prepared according to methods known from the literature (compare, for example, Weygand/Hilgetag, *Org. Chemische Experimentierkunst* (The Art of Experimentation in Organic Chemistry), page 691, page 704 and page 645, 4th edition, 1970, Verlag J. A. Barth, Leipzig).

The following starting materials are representative of those materials which may be used according to the present invention: methanesulphonic acid chloride, ethanesulphonic acid chloride, butanesulphonic acid chloride, benzenesulphonic acid chloride, p-toluenesulphonic acid chloride, 4-chlorobenzenesulphonic acid chloride, 3-chlorobenzenesulphonic acid chloride, 4-fluorobenzenesulphonic acid chloride, 3,4-dichlorobenzenesulphonic acid chloride and 3-chloro-4-methylbenzenesulphonic acid chloride.

Suitable diluents are all inert solvents. These preferentially include hydrocarbon atoms such as benzene, toluene and xylene, halogenohydrocarbons, such as methylene chloride, chloroform, carbon tetrachloride and chlorobenzene, ethers, such as tetrahydrofurane, dioxane and glycol dimethyl ether, amides, such as dimethylformamide, dimethylacetamide, N-methylpyrrolidone and hexamethylphosphoric acid triamide, sulphoxides, such as dimethylsulphoxide, sulphones, such as sulpholane, and bases, such as pyridine, picoline, collidine, lutidine and quinoline.

Suitable basic auxiliaries are inorganic and organic bases. These preferentially include alkali metal hydroxides and alkali metal carbonates, such as sodium hydroxide or potassium carbonate, and tert.-amines, such as triethylamine or pyridine.

The reaction temperatures can be varied within a wide range. In general, the reaction is carried out at between −10° and 150° C., preferably between 0° and 100° C. It is carried out under normal pressure, but can also be carried out under a higher pressure in closed vessels.

In carrying out the process according to the invention, one mol of the 5-pyrazolone derivative is reacted with 1 to 5 mols of the carboxylic acid derivative, carbonic acid derivative or sulphonic acid derivative in an inert diluent, if appropriate in the presence of molar amounts of a basic auxiliary, such as triethylamine or pyridine. The compounds according to the invention, which in most cases are obtained in a crystalline form after removing the diluent, can easily be prepared in a pure form by recrystallization from a suitable solvent.

The following compounds are representative of those of the present invention: 5-acetoxy-3-trifluoromethyl-4-phenyl-1-(α-methyl-3,4-dichlorobenzyl)-pyrazole, 5-acetoxy-3-methyl-4-phenyl-1-(α-methyl-3-chloro-4-methyl)-pyrazole, 5-acetoxy-3-ethyl-4-phenyl-1-(α-methyl-3-chloro-4-methylbenzyl)-pyrazole, 5-acetoxy-3-methyl-4-(4-chlorophenyl)-1-(α-naphthyl-(2)-ethyl)-pyrazole, 5-acetoxy-4-phenyl-1-(α-methyl-3,4-dichlorobenzyl)-pyrazole, 5-acetoxy-4-phenyl-1-(α-methyl-4-fluorobenzyl)-pyrazole, 5-acetoxy-3,4-diphenyl-1-(α-methyl-3,4-ditrifluoromethylbenzyl)-pyrazole, 5-propionyloxy-4-phenyl-1-(α-propyl-3,4-dichlorobenzyl)-pyrazole, 5-propionyloxy-3,4-diphenyl-1-(α-methyl-3,4-dichlorobenzyl)-pyrazole, 5-propionyloxy-3-isopropyl-4-(4-chlorphenyl)-1-(α-methyl-3,4-dichlorobenzyl)-pyrazole, 5-n-butyryloxy-3-methyl-4-phenyl-1-(α-methyl-3,4-dichlorobenzyl)-pyrazole, 5-trimethylacetoxy-3-methyl-4-phenyl-1-(α-methyl-3-chloro-4-methylbenzyl)-pyrazole, 5-isovaleryloxy-3-methyl-4-phenyl-1-(α-methyl-3,4-difluorobenzyl)-pyrazole, 5-trifluoroacetoxy-3-methyl-4-phenyl-1-(α-methyl-3,4-dichlorobenzyl)-pyrazole, 5-trifluoroacetoxy-3,4-diphenyl-1-(α-methyl-3,4-dichlorobenzyl)-pyrazole, 5-trifluoroacetoxy-3,4-diphenyl-1-(α-methyl-3,4-ditrifluoromethylbenzyl)-pyrazole, 5-chloroacetoxy-3-methyl-4-phenyl-1-(α-methyl-3,4-dichlorobenzyl)-pyrazole, 5-chloroacetoxy-3,4-diphenyl-1-(α-methyl-3-chloro-4-methylbenzyl)-pyrazole, 5-dichloroacetoxy-3-methyl-4-phenyl-1-(α-methyl-3,4-dichlorobenzyl)-pyrazole, 5-dichloroacetoxy-3,4-diphenyl-1-(α-methyl-3-chloro-4-methylbenzyl)-pyrazole, 5-(3-chloropropionyloxy)-3-methyl-4-phenyl-1-(α-methyl-3,4-dichlorbenzyl)-pyrazole, 5-(2-methoxyacetoxy)-3,4-diphenyl-1-(α-methyl-3,4-dichlorobenzyl)-pyrazole, 5-(2-dimethylaminoacetoxy)-3-ethyl-4-phenyl-1-(α-methyl-3-chloro-4-methylbenzyl)-pyrazole, 5-(2-fluorobenzoyloxy)-3,4-diphenyl-1-(α-methyl-3,4-dichlorobenzyl)-pyrazole, 5-(3-fluorobenzoyloxy)-3-isopropyl-4-(4-chlorophenyl)-1-(α-ethyl-3,4-difluorobenzylpyrazole, 5-(3-chlorobenzoyloxy)-3-methyl-4-benzyl-1-(α-methyl-3-trifluoromethylbenzyl)-pyrazole, 5-(4-trifluoromethylsulphonylbenzoyloxy)-3-methyl-4-benzyl-1-(α-naphthyl-(2)-ethyl)-pyrazole, 5-(pyrryl-(2)-carbonyloxy)-3-methyl-4-phenyl-1-(α-methyl-3,4-dichlorobenzyl)-pyrazole, 5-(pyrryl-(3)-carbonyloxy)-3,4-diphenyl-1-(α-methyl-3-chloro-4-methylbenzyl)-pyrazole, 5-(thienyl-(2)-carbonyloxy)-3-methyl-4-phenyl-1-(α-pyridyl-(2)-ethyl)-pyrazole, 5-(thienyl-(3)-carbonyloxy)-3-methyl-4-phenyl-1-(α-methyl-3,4-difluorobenzyl)-pyrazole, 5-(furyl-(2)-carbonyloxy)-3-(4-chlorophenyl)-4-phenyl-1-(α-methyl-3,4-dichlorobenzyl)-pyrazole, 5-(furyl-(3)-carbonyloxy)-3-methyl-4-phenyl-1-(α-methyl-4-fluorobenzyl)pyrazole, 5-(pyrazolyl-(3)-carbonyloxy)-3,4-diphenyl-1-(α-methyl-3,4-dichlorobenzyl)-pyrazole, 5-(pyrazolyl-(4)-carbonyloxy)-3-methyl-4-(4-chlorophenyl)-1-(α-methyl-4-chlorobenzyl)-pyrazole, 5-(4-methyl-pyrazolyl-(3)-carbonyloxy)-3-n-propyl-4-phenyl-1-(α-pyridyl-(3)-ethyl)-pyrazole, 5-(4-methylimidazolyl-(2)-carbonyloxy)-3-ethyl-4-phenyl-1-(α-methyl-3,4-dichlorobenzyl)-pyrazole, 5-(imidazolyl-(2)-carbonyloxy)-4-phenyl-1-(α-methyl-3,4-dichlorobenzyl)-pyrazole, 5-(thiazolyl-(2)-carbonyloxy)-3,4-diphenyl-1-(α-methyl-3,4-dichlorobenzyl)-pyrazole, 5-(5-nitrothiazolyl-(2)-carbonyloxy)-3-methyl-4-(3-chlorophenyl)-1-(α-naphthyl-(2)-ethyl)-pyrazole, 5-(oxazolyl-(4)-carbonyloxy)-3,4-diphenyl-1-(α-methyl-3,4-dichlorobenzyl)-pyrazole, 5-(oxazolyl-(5)-carbonyloxy)-3-methyl-4-benzyl-1-(α-methyl-4-fluorobenzyl)-pyrazole, 5-(isoxazolyl-(3)-carbonyloxy)-3-phenyl-4-benzyl-1-(α-methyl-3,4-dichlorobenzyl)-pyrazole, 5-(isoxazolyl-(4)-carbonyloxy)-3,4-diphenyl-1-(α-methyl-4-chlorobenzyl)-pyrazole, 5-(5-methylisoxazolyl-(3)-carbonyloxy)-3-trifluoromethyl-4-benzyl-1-(α-methyl-3,4-dichlorobenzyl)-pyrazole, 5-(5-methylisoxazolyl-(3)-carbonyloxy)-3-ethyl-4-benzyl-1-(α-methyl-3-chloro-4-methylbenzyl)-pyrazole, 5-(3-fluoropicolinoyloxy)-3,4-diphenyl-1-(α-methyl-3,4-dichlorobenzyl)-pyrazole, 5-(nicotinoyloxy)-3-n-propyl-4-(4-methylphenyl)-1-(α-methyl-3,4-difluorobenzyl)-pyrazole, 5-(4)fluoronicotinoyloxy)-4-benzyl-1-(α-methyl-3,4-dichlorobenzyl)-pyrazole, 5-(dihydrofuryl-(2)-carbonyloxy)-3-(4-chlorophenyl)-4-phenyl-1-(α-methyl-3,4-dichlorobenzyl)-pyrazole, 5-(tetrahydrofuryl-(2)-carbonyloxy)-3,4-diphenyl-1-(α-methyl-3,4-dichlorobenzyl)-pyrazole, 5-(1-methyl-1,4,5,6-tetrahydropyridyl-(3)-carbonyloxy)-3-methyl-4-phenyl-1-(α-methyl-3,4-dichlorobenzyl)-pyrazole, 5-(1-methylpiperidyl-(2)-carbonyloxy)-3-methyl-4-(2-methylphenyl)-1-(α-methyl-3,4-dichlorobenzyl)-pyrazole, 5-(1-methylpiperidyl-(3)-carbonyloxy)-3-methyl-4-(4-methylphenyl)-1-(α-methyl-4-chlorobenzyl)-pyrazole, 5-(1-methylpiperidyl-(4)-carbonyloxy)-3-methyl-4-(3-methyl-4-chlorophenyl)-1-(α-methyl-4-fluorobenzyl)-pyrazole, 5-(tetrahydropyranyl-(2)-carbonyloxy)-3-methyl-4-(3-methylphenyl)-1-(α-methyl-3,4-dichlorobenzyl)-pyrazole, 5-(tetrahydrothiopyranyl-(2)-carbonyloxy)-3-methyl-4-phenyl-1-(α-methyl-3,4-dichlorobenzyl)-pyrazole, 5-(1,2,3-thiadiazolyl-(4)-carbonyloxy)-3-methyl-4-(4-methylphenyl)-1-(α-methyl-3,4-dichlorobenzyl)-pyrazole, 5-(morpholinocarbonyloxy)-3-methyl-4-phenyl-1-(α-methyl-3,4-dichlorobenzyl)-pyrazole, 5-(isonicotinoyloxy)-3-isopropyl-4-(3-chlorophenyl)-1-(α-methyl-3,4-dichlorobenzyl)-pyrazole, 5-(2,6-dichloroisonicotinoyloxy)-3-methyl-4-phenyl-1-(α-methyl-3,4-dichlorobenzyl)-pyrazole, 5-(2,6-dichloroisonicotinoyloxy)-3,4-diphenyl-1-(α-methyl-3,4-dichlorobenzyl)-pyrazole, 5-(pyridazinyl-(3)-carbonyloxy)-3-phenyl-4-benzyl-1-(α-methyl-3,4-dichlorobenzyl)-pyrazole, 5-(pyridazinyl-(4)-carbonyloxy)-3-isopropyl-4-benzyl-1-(α-methyl-4-fluorobenzyl)-pyrazole, 5-(pyrimidinyl-(4)-carbonyloxy)-3,4-diphenyl-1-(α-methyl-3,4-dichlorobenzyl)-pyrazole, 5-(pyrimidinyl-(2)-carbonyloxy)-3-ethyl-4-(p-methoxyphenyl)-1-(α-methyl-4-fluorobenzyl)-pyrazole, 5-(pyrimidinyl-(5)-carbonyloxy)-3-n-propyl-4-(p-fluorophenyl)-1-(α-methyl-4-chlorobenzyl)-pyrazole, 5-(pyrazinyl-(2)-carbonyloxy)-3-ethyl-4-phenyl-1-(α-ethyl-3,4-tetramethylenebenzyl)-pyrazole, 5-(4-methylpiperazinyl-(1)-carbonyloxy)-3,4-diphenyl-1-(α-methyl-3,4-dichlorobenzyl)-pyrazole, 5-(1-ethylpiperidyl-(2)-carbonyloxy)-3,4-diphenyl-1-(α-methyl-3,4-dichlorobenzyl)-pyrazole, 5-(1-ethylpiperidyl-(2)-carbonyloxy)-3,4-diphenyl-1-(α-methyl-3,4-tetramethylenebenzyl)-pyrazole, 5-(1-ethylpiperidyl-(3)-carbonyloxy)-3-methyl-4-phenyl-1-(α-methyl-4-chlorobenzyl)-pyrazole, 5-(1-ethylpiperidyl-(3)-carbonyloxy)-3-methyl-4-phenyl-1-(α-methyl-3,4-dichlorobenzyl)-pyrazole, 5-(3-methylphenylsulphonyloxy)-3-methyl-4-phenyl-1-(α-methyl-3-chlorobenzyl)-pyrazole, 5-(3,4-dimethylphenylsulphonyloxy)-3-methyl-4-(4-chlorophenyl)-1-(α-methyl-3,4-dichlorobenzyl)-pyrazole, 5-(3-chlorophenylsulphonyloxy)-1-methyl-4-phenyl-1-(pyridyl-(3)-ethyl)-pyrazole, 5-(2-fluorophenylsulphonyloxy)-3,4-diphenyl-1-(α-methyl-3-trifluoromethylbenzyl)-pyrazole, 5-(4-trifluoromethylsulphenylphenylsulphonyloxy)-3-methyl-4-phenyl-1-(α-naphthyl-(2)-ethyl)-pyrazole, 5-(fluorophenylsulphonyloxy)-3-methyl-4-phenyl-1-(α-methyl-3,4-tetramethylenebenzyl)-pyrazole, 5-(4-fluorophenylsulphonyloxy)-3-methyl-4-(4-methylphenyl)-1-(α-methyl-3,4-tetramethylenebenzyl)-pyrazole and 5-(3,4-dinitrophenylsulphonyloxy)-3-methyl-4-phenyl-1-(α-methyl-3-chloro-4-methylbenzyl)-pyrazole.

The pharmaceutical compositions of the present invention contain a major or minor amount e.g. 0.1 to 99.5%, preferably 0.5 to 90%, of active ingredient as above defined in combination with a pharmaceutically acceptable nontoxic inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 0.01 to 500 mg/kg of body weight per day. In some instances a sufficient therapeutic effect can be obtained at a lower dose, while in others a larger dose will be required.

The preferred daily dose is 0.5 mg to 10 g of active agent.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinylpyrrolidone, a solution retardant such as paraffin, a resorption accellerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polishcoating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

While routes of administration include oral, parenteral (i.e., intramuscular, intraperitoneal and intravenous) and rectal, oral and parenteral administration are particularly preferred.

The preferred daily dose, in the case of parenteral administration, is 0.01 to 50 mg/kg, preferably 0.1 to 10 mg/kg of body weight daily; while for oral administration the preferred daily dose is about 0.1 to 500 mg/kg, preferably 0.5 to 100 mg/kg, of body weight daily.

The preferred pharmaceutical compositions are therefore those in a form suitable for oral administration, such as tablets and suspensions, and those suitable for parenteral application, such as solutions and suspensions, to effect diuresis, saluresis and to treat hypertension by eliminating water and salts and also are useful for the treatment of prophylaxis of thromboembolic diseases. In addition, the compounds are useful for the treatment of oedemacious and hypertonic conditions and for flooding out of toxic substances so that they may be used in the case of acute kidney failure.

The following formulation is representative of those of the present invention: 200 g of 5-(4-fluorobenzoyloxy)-3-methyl-4-phenyl-1-(α-methyl-3,4-dichlorobenzyl)-pyrazole are ground to a powder which is mixed with 300 g of lactose and 200 g of potato starch and, after moistening with an aqueous gelatine solution, the mixture is granulated by passing through a sieve. After drying, 60 g of talc and 5 g of sodium lauryl-sulphate are added. From this mixture about 10,000 tablets each containing 20 mg of active compound are pressed.

To demonstrate the antithrombotic action of the compounds according to the invention, the substance described in Example 1 was administered to rats.

The left jugular vein of rats weighing 170 to 180 g was exposed under ether narcosis and supercooled to −12° C. for 2 minutes to stimulate thromb formation. The thromb was isolated from the vein 4 hours later, and was weighed. The test animals were given the test preparation in tragacanth mucilage immediately before supercooling the wall of the blood vessel. As a result, the protective antithrombotic activity was tested in the first 4 hours after stimulating thromb formation.

The results of the investigations using the compounds according to the invention are shown in the table which follows:

|  | Control on animals without active compound | Animals treated with the compound according to the invention (10 mg/kg, administered orally) |
|---|---|---|
| Thromb size in μg, mean value | 115 ± 12 | 51 ± 10 |
| Number of experiments | 14 | 12 |
| Inhibition in % | 0 | 56% |

The results show that the compounds according to the invention significantly inhibit the formation of venous thrombs.

After a 4 hour period of action, the size of the thrombs has been reduced by 56%.

The remaining compounds show comparable properties and can therefore be used for the prophylaxis of thrombembolic diseases.

In addition to the inhibiting action on the formation of thrombs, the compounds according to the invention are also distinguished by a very powerful thrombolytic action. Thrombotic deposits already formed are redispersed under the influence of the compound. Corresponding thrombolytic effects were hitherto only achievable by repeated intravenous administration of toxic fibrinolytics such as streptokinase and urokinase, while the compounds according to the invention are administered orally and only once daily.

The following nonlimitative examples more particularly illustrate the present invention.

EXAMPLE 1

5-(4-Fluorobenzoyloxy)-3-methyl-4-phenyl-1-(α-methyl-3,4-dichlorobenzyl)-pyrazole

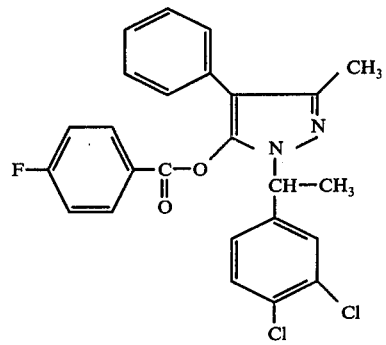

0.1 mol (34.7 g) of 3-methyl-4-phenyl-1-(α-methyl-3,4-dichlorobenzyl)-5-pyrazolone was dissolved in 300 ml of absolute dioxane. After adding 15 ml of triethylamine, 0.11 mol (17 g) of p-fluorobenzoyl chloride in dioxane was added dropwise. After heating for several hours under reflux, the reaction batch was worked up as follows.

The organic phase obtained after cooling, and after filtering off the precipitates of crystalline salt was concentrated, the residue was taken up in methylene chloride, and the methylene chloride solution was repeatedly extracted by shaking with water and was dried with magnesium sulphate.

The oily residue obtained after concentrating the methylene chloride phase became crystalline on trituration with methanol. The crystalline crude product was recrystallized from ethyl acetate. Melting point: 112°–114° C.; yield: 76% of theory.

The following products were obtained analogously to the procedure described in Preparation Example 1:

EXAMPLE 2

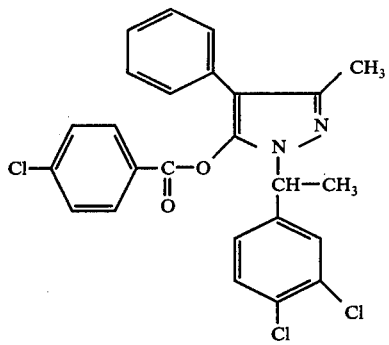

5-(4-Chlorobenzoyloxy)-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and p-chlorobenzoyl chloride.

Melting point: 107°–109° C. (ethanol); yield: 83% of theory.

EXAMPLE 3

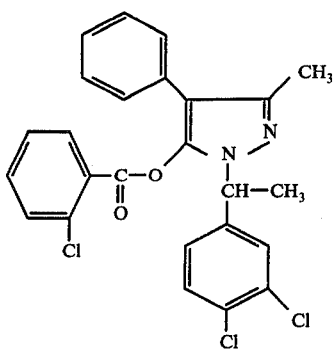

5-(2-Chlorobenzoyloxy)-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and 2-chlorobenzoyl chloride.

Melting point: 123°–125° C. (ethanol); yield: 89% of theory.

EXAMPLE 4

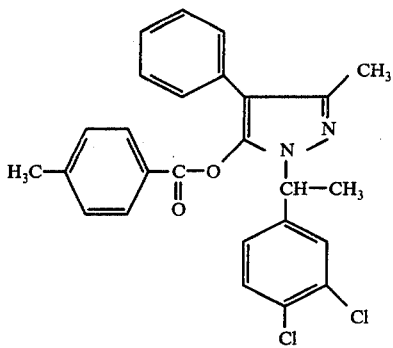

5-(4-Methylbenzoyloxy)-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and 4-methylbenzoyl chloride.

Melting point: 108°–110° C. (ethyl acetate); yield: 86% of theory.

EXAMPLE 5

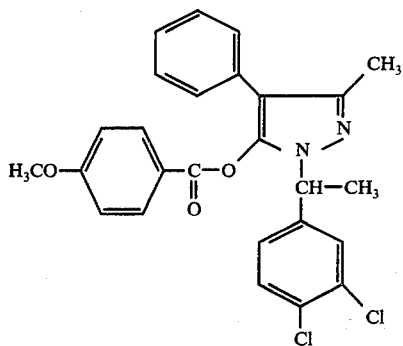

5-(4-Methoxybenzoyloxy)-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and 4-methoxy-benzoyl chloride.

Melting point: 121°–123° C. (ethyl acetate); yield: 78% of theory.

EXAMPLE 6

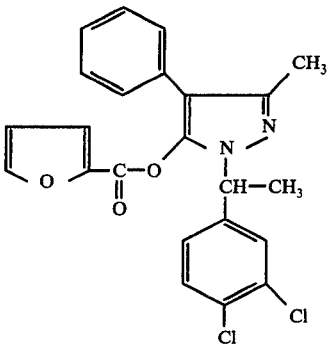

5-(Furyl-2-carbonyloxy)-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and furane-2-carboxylic acid chloride.

Melting point: 80°–82° C. (ethyl acetate); yield: 53% of theory.

EXAMPLE 7

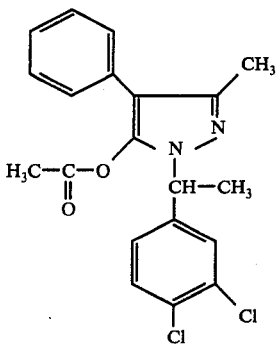

5-Acetoxy-3-methyl-4-phenyl-1-(α-methyl-3,4-dichlorobenzyl)-pyrazole was obtained from 3-methyl-4-phenyl-1-(α-methyl-3,4-dichlorobenzyl)-5-pyrazolone and acetyl chloride.

Melting point: 93°–95° C. (ether); yield: 55% of theory.

EXAMPLE 8

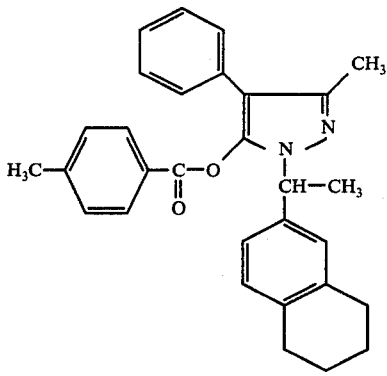

5-(4-Methylbenzoyloxy)-3-methyl-4-phenyl-1-(α-methyl-3,4-tetramethylenebenzyl)-pyrazole was obtained from 3-methyl-4phenyl-1-(α-methyl-3,4-tetramethylenebenzyl)-5-pyrazolone and 4-methylbenzoyl chloride.

Melting point: 109°-110° C. (ethanol); yield: 78% of theory.

EXAMPLE 9

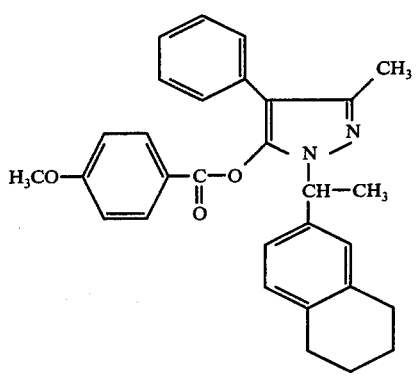

5-(4-Methoxybenzoyloxy)-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and 4-methoxybenzoyl chloride.

Melting point: 136°-138° C. (ethanol); yield: 92% of theory.

EXAMPLE 10

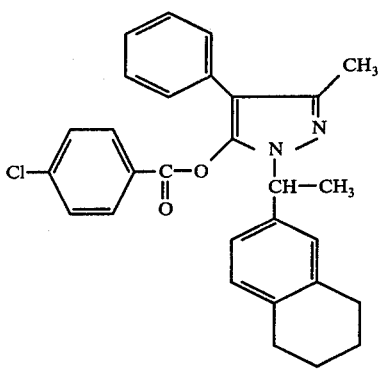

5-(4-Chlorobenzoyloxy)-3-methyl-4-phenyl-1-(α-methyl-3,4-tetramethylenebenzyl)-pyrazole was obtained from 3-methyl-4-phenyl-1-(α-methyl-3,4-tetramethylene-benzyl)-5-pyrazolone and 4-chlorobenzoyl chloride.

Melting point: 114°-115° C. (ethanol/ether); yield: 84% of theory.

EXAMPLE 11

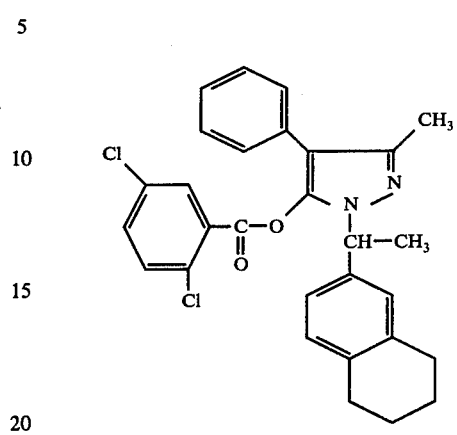

5-(2,5-Dichlorobenzoyloxy)-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and 2,5-dichlorobenzoyl chloride.

Melting point: 152°-154° C. (ethanol): yield: 81% of theory.

EXAMPLE 12

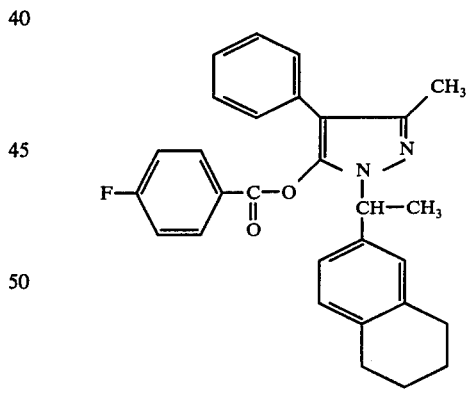

5-(4-Fluorobenzoyloxy)-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and 4-fluorobenzoyl chloride.

Melting point: 133°-135° C. (ethanol); yield: 79% of theory.

EXAMPLE 13

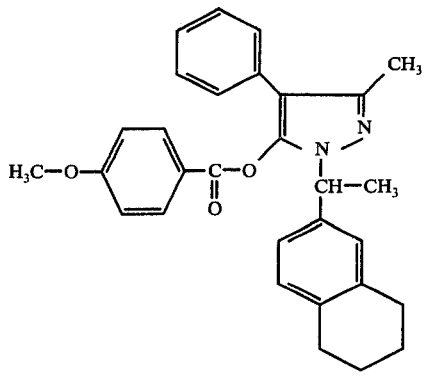

5-(4-Methoxybenzoyloxy)-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and 4-methoxybenzoyl chloride.

Melting point: 136°–138° C. (ethanol); yield: 84% of theory.

EXAMPLE 14

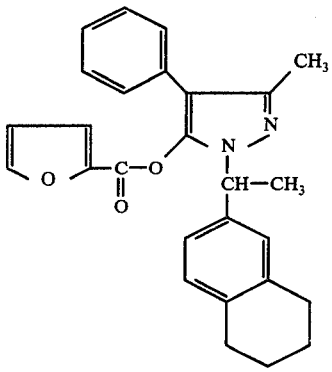

5-(Furyl-2-carbonyloxy)-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and furane-2-carboxylic acid chloride.

Melting point: 94°–96° C. (methanol); yield: 81% of theory.

EXAMPLE 15

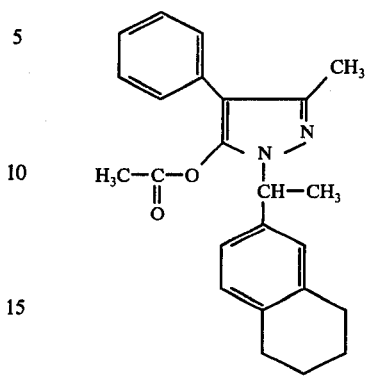

5-Acetoxy-3-methyl-4-phenyl-1-(α-methyl-3,4-tetramethylenebenzyl)-pyrazole was obtained from 3-methyl-4-phenyl-1-(α-methyl-3,4-tetramethylenebenzyl)-5-pyrazolone and acetyl chloride.

Melting point: 66°–68° C. (ether); yield: 52% of theory.

EXAMPLE 16

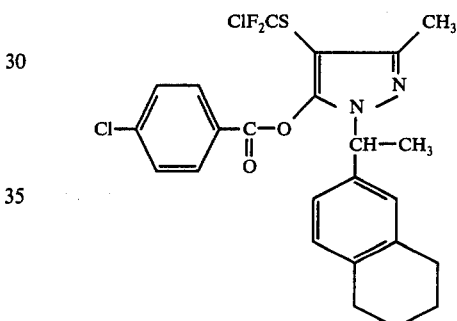

5-(4-Chlorobenzoyloxy)-3-methyl-4-(chlorodifluoromethylthio)-1-(α-methyl-3,4-tetramethylene-benzyl-pyrazole was obtained from 3-methyl-4-(chlorodifluoromethylthio)-1-(α-methyl-3,4-tetramethylenebenzyl)-5-pyrazolone and 4-chlorobenzoyl chloride.

Melting point: 83°–85° C. (ethanol); yield: 89% of theory.

What is claimed is:

1. A pharmaceutical composition useful for effecting diuresis and saluresis in humans and animals and for treating hypertension and thromboses in humans and animals which comprises a diuretically effective amount, a saluretically effective amount, an anti-hypertensively effective amount or an antithrombotically effective amount of a compound of the formula

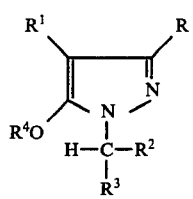

wherein
R is hydrogen or lower alkyl;

$R^1$ is haloalkylthio of 1 to 4 carbon atoms in the alkyl moiety and 1 to 3 halo atoms;

$R^2$ is lower alkyl;

$R^3$ is aryl of 6 to 10 carbon atoms unsubstituted or substituted by 1 to 3 of the same or different substituents selected from the group consisting of alkyl of 1 to 4 carbon atoms, alkenyl of 2 to 4 carbon atoms, alkoxy of 1 to 4 carbon atoms, halo, trifluoromethyl, trifluoromethoxy, mono- or di-alkylamino of 1 to 4 carbon atoms in each alkyl moiety, nitro, cyano, carboxamido, sulphonamido and $SO_n$-alkyl of 1 to 4 carbon atoms in the alkyl moiety and wherein $n$ is 0 to 2; or phenyl having fused thereto a 5- to 7-membered isocyclic ring; and $R^4$ is $R^5CO$ wherein $R^5$ is lower alkyl, cycloalkyl of 5 to 7 carbon atoms, halo (lower alkyl), lower alkoxy, lower alkythio, halo(lower alkoxy), halo(lower alkythio), lower alkoxy(lower alkyl), mono- or di(lower alkylamino), phenyl substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, carboxamido, sulphonamido, $SO_n$-(lower alkyl) wherein $n$ is 0 to 2, and $SO_n$-$CF_3$ wherein $n$ is 0 to 2 or phenyl having fused thereto a 5- to 7-membered isocyclic ring, in combination with a pharmaceutically acceptable carrier.

2. A composition according to claim 1 wherein
R is alkyl of 1 to 4 carbon atoms; and $R^4$ is $R^5CO$ wherein $R^5$ is alkyl of 1 to 4 carbon atoms, cycloalkyl of 5 to 7 carbon atoms, haloalkyl of 1 to 4 carbon atoms in the alkyl moiety, lower alkoxy, alkylthio of 1 to 4 carbon atoms in the alkyl moiety, haloalkylthio of 1 to 4 carbon atoms in the alkyl moiety, alkoxyalkyl of 1 to 4 carbon atoms in the alkoxy and in the alkyl moieties, mono- or di-alkylamino of 1 to 4 carbon atoms in the alkyl moiety, phenyl substituted by 1 to 3 substituents selected from the group consisting of alkyl of 1 to 4 carbon atoms, alkoxy of 1 to 4 carbon atoms, fluoro, chloro, bromo, trifluoromethyl, trifluoromethoxy, nitro, cyano, carboximido, sulphonamideo, $SO_n$-alkyl of 1 to 4 carbon atoms in the alkyl moiety wherein $n$ is 0 to 2, and $SO_n$—$CF_3$ wherein $n$ is 0 to 2; or phenyl having fused thereto a 5- to 7-membered isocyclic ring.

3. A composition according to claim 1 wherein
R is hydrogen or alkyl of 1 to 4 carbon atoms;

$R^1$ is chloroalkylthio of 1 to 4 carbon atoms in the alkyl moiety and 1 to 3 chloro atoms;

$R^2$ is alkyl of 1 to 4 carbon atoms;

$R^3$ is phenyl substituted by 1 or 2 of the same or different substituents selected from the group consisting of alkyl of 1 to 8 carbon atoms, alkenyl of 2 to 8 carbon atoms, alkoxy of 1 to 6 carbon atoms, cycloalkyl of 5 to 7 carbon atoms, cycloalkenyl of 5 to 7 carbon atoms, fluoro, chloro, bromo, trifluoromethyl, trifluoromethoxy, nitro, cyano, dialkylamino of 1 to 4 carbon atoms in each alkyl moiety, carboxamido, sulphonamido or carboxamido or sulphonamido wherein 1 or both of the hydrogen atoms are substituted by 1 or 2 alkyl moieties of 1 to 4 carbon atoms, and $SO_n$-alkyl of 1 to 4 carbon atoms in the alkyl moiety wherein $n$ is 0 or 2; or phenyl having fused thereto a saturated 5- to 7-membered isocyclic ring.

4. A composition according to claim 3 wherein
$R^3$ is tetramethylenephenyl.

5. A composition according to claim 1 wherein
$R^4$ is alkylcarbonyl of 1 to 6 carbon atoms in the alkyl moiety; alkoxycarbonyl of 1 to 6 carbon atoms in the alkoxy moiety; haloalkylcarbonyl of 1 to 6 carbon atoms in the alkyl moiety and 1 to 3 halo atoms; alkoxyalkylcarbonyl of 1 to 6 carbon atoms in the alkoxy and alkyl moieties; benzoyl nuclear substituted by 1 or 2 substituents selected from the group consisting of alkyl of 1 to 4 carbon atoms, halo, trifluoromethyl, trifluoromethoxy and nitro, or by 1 trifluoromethylsulphonyl; or dialkylaminoalkylcarbonyl of 1 to 4 carbon atoms in each of the alkyl moieties.

6. A composition according to claim 1 wherein
R is hydrogen or alkyl of 1 to 3 carbon atoms;

$R^2$ is methyl or ethyl;

$R^3$ is phenyl substituted by 2 halo atoms; or tetramethylenephenyl; and $R^4$ is acetyl; or benzoyl nuclear substituted by 1 or 2 substituents selected from the group consisting of alkyl of 1 or 2 carbon atoms, alkoxy of 1 or 2 carbon atoms, fluoro, chloro, trifluoromethyl, nitro and cyano.

7. A composition according to claim 6 wherein
$R^4$ is acetyl; or benzoyl nuclear substituted by 1 or 2 substituents selected from the group consisting of methyl, methoxy, fluoro, chloro, trifluoromethyl, nitro and cyano.

8. A composition according to claim 1 wherein
R is alkyl of 1 to 3 carbon atoms;

$R^2$ is methyl or ethyl;

$R^3$ is phenyl substituted by 1 or 2 of the same or different substituents selected from the group consisting of alkyl of 1 or 2 carbon atoms, chloro, fluoro and trifluoromethyl; naphthyl; or tetramethylenephenyl; and $R^4$ is $R^5CO$ wherein $R^5$ is alkyl of 1 to 4 carbon atoms, haloalkyl of 1 to 4 carbon atoms in the alkyl moiety and 1 to 3 halo atoms selected from the group consisting of chloro and fluoro; alkoxy of 1 to 4 carbon atoms; mono- or di-alkylamino of 1 to 4 carbon atoms in each alkyl moiety; or phenyl substituted by 1 to 3 substituents selected from the group consisting of alkyl of 1 or 4 carbon atoms, alkoxy of 1 or 4 carbon atoms, fluoro, chloro, and trifluoromethylsulphonyl.

9. A composition according to claim 8 wherein
$R^4$ is $R^5CO$ wherein $R^5$ is alkyl of 1 or 2 carbon atoms, haloalkyl of 1 or 2 carbon atoms in the alkyl moiety and 1 to 3 halo atoms selected from the group consisting of chloro and fluoro; alkoxy of 1 or 2 carbon atoms; mono- or di-alkylamino of 1 or 2 carbon atoms in each alkyl moiety; or phenyl substituted by 1 to 3 substituents selected from the group consisting of alkyl of 1 or 2 carbon atoms, alkoxy of 1 or 2 carbon atoms, fluoro, chloro and trifluoromethylsulphonyl.

10. A composition according to claim 1 wherein
R is alkyl of 1 or 2 carbon atoms;

$R^2$ is methyl;

$R^3$ is dichlorophenyl or tetramethylenephenyl; and $R^4$ is acetyl, methylbenzoyl, methoxybenzoyl, chlorobenzoyl, fluorobenzoyl or dichlorobenzoyl.

11. A composition according to claim 1 wherein the compound is

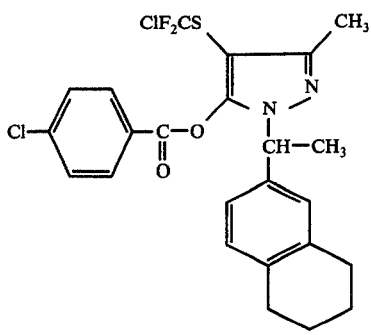

12. A method of effecting diuresis and saluresis in humans and animals and treating hypertension in humans and animals which comprises administering to a human or animal in need thereof a diuretically effecdive amount, a saluretically effective amount or an antihypertensively effective amount of a compound of the formula

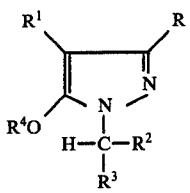

wherein
R is hydrogen or lower alkyl;
$R^1$ is haloalkylthio of 1 to 4 carbon atoms in the alkyl moiety and 1 to 3 halo atoms;
$R^2$ is lower alkyl;
$R^3$ is aryl of 6 to 10 carbon atoms unsubstituted or substituted by 1 to 3 of the same or different substituents selected from the group consisting of alkyl of 1 to 4 carbon atoms, alkenyl of 2 to 4 carbon atoms, alkoxy of 1 to 4 carbon atoms, halo, trifluoromethyl, trifluoromethoxy, mono- or di-alkylamino of 1 to 4 carbon atoms in each alkyl moiety, nitro, cyano, carboxamido, sulphonamido and $SO_n$-alkyl of 1 to 4 carbon atoms in the alkyl moiety and wherein $n$ is 0 to 2; or phenyl having fused thereto a 5- to 7-membered isocyclic ring; and
$R^4$ is $R^5CO$ wherein $R^5$ is lower alkyl, cycloalkyl of 5 to 7 carbon atoms, halo(lower alkyl), lower alkoxy, lower alkylthio, halo(lower alkoxy), halo(lower alkylthio), lower alkoxy(lower alkyl), mono- or di(lower alkylamino), phenyl substituted by 1 to 3 substituents selected from the group consisting of alkyl of 1 to 4 carbon atoms, alkoxy of 1 to 4 carbon atoms, halo, trifluoromethyl, trifluoromethoxy, nitro, cyano, carboxamido, sulphonamido, $SO_n$-(lower alkyl) wherein $n$ is 0 to 2, and $SO_n$—$CF_3$ wherein $n$ is 0 to 2; or phenyl having fused thereto a 5- to 7-membered isocyclic ring, in combination with a pharmaceutically acceptable carrier.

13. A method according to claim 12 wherein
R is alkyl of 1 to 4 carbon atoms; and
$R^4$ is $R^5CO$ wherein $R^5$ is alkyl of 1 to 4 carbon atoms, cycloalkyl of 5 to 7 carbon atoms, haloalkyl of 1 to 4 carbon atoms in the alkyl moiety, lower alkoxy, alkylthio of 1 to 4 carbon atoms in the alkyl moiety, haloalkylthio of 1 to 4 carbon atoms in the alkyl moiety, alkoxyalkyl of 1 to 4 carbon atoms in the alkoxy and in the alkyl moieties, mono- or di-alkylamino of 1 to 4 carbon atoms in the alkyl moiety, phenyl substituted by 1 to 3 substituents selected from the group consisting of alkyl of 1 to 4 carbon atoms, alkoxy of 1 to 4 carbon atoms, fluoro, chloro, bromo, trifluoromethyl, trifluoromethoxy, nitro, cyano, carboximido, sulphonamideo, $SO_n$-alkyl of 1 to 4 carbon atoms in the alkyl moiety wherein $n$ is 0 to 2, and $SO_n$—$CF_3$ wherein $n$ is 0 to 2; or phenyl having fused thereto a 5- to 7-membered isocyclic ring.

14. A method according to claim 12 wherein
R is hydrogen or alkyl of 1 to 4 carbon atoms;
$R^1$ is chloroalkylthio of 1 to 4 carbon atoms in the alkyl moiety and 1 to 3 chloro atoms;
$R^2$ is alkyl of 1 to 4 carbon atoms;
$R^3$ is phenyl substituted by 1 or 2 of the same or different substituents selected from the group consisting of alkyl of 1 to 8 carbon atoms, alkenyl of 2 to 8 carbon atoms, alkoxy of 1 to 6 carbon atoms, cycloalkyl of 5 to 7 carbon atoms, cycloalkenyl of 5 to 7 carbon atoms, fluoro, chloro, bromo, trifluoromethyl, trifluoromethoxy, nitro, cyano, dialkylamino of 1 to 4 carbon atoms in each alkyl moiety, carboxamido, sulphonamido or carboxamido or sulphonamido wherein 1 or both of the hydrogen atoms are substituted by 1 or 2 alkyl moieties of 1 to 4 carbon atoms, and $SO_n$-alkyl of 1 to 4 carbon atoms in the alkyl moiety wherein $n$ is 0 or 2; or phenyl having fused thereto a saturated 5- to 7-membered isocyclic ring.

15. A method according to claim 12 wherein
$R^3$ is tetramethylenephenyl.

16. A method according to claim 12 wherein
$R^4$ is alkylcarbonyl of 1 to 6 carbon atoms in the alkyl moiety; alkoxycarbonyl of 1 to 6 carbon atoms in the alkoxy moiety; haloalkylcarbonyl of 1 to 6 carbon atoms in the alkyl moiety and 1 to 3 halo atoms; alkoxyalkylcarbonyl of 1 to 6 carbon atoms in the alkoxy and alkyl moieties; benzoyl nuclear substituted by 1 or 2 substituents selected from the group consisting of alkyl of 1 to 4 carbon atoms, halo, trifluoromethyl, trifluoromethoxy and nitro, or by 1 trifluoromethylsulphonyl; or dialkylaminoalkylcarbonyl of 1 to 4 carbon atoms in each of the alkyl moieties.

17. A method according to claim 12 wherein
R is hydrogen or alkyl of 1 to 3 carbon atoms;
$R^2$ is methyl or ethyl;
$R^3$ is phenyl substituted by 2 halo atoms; or tetramethylenephenyl; and
$R^4$ is acetyl; or benzoyl nuclear substituted by 1 or 2 substituents selected from the group consisting of alkyl of 1 or 2 carbon atoms, alkoxy of 1 or 2 carbon atoms, fluoro, chloro, trifluoromethyl, nitro and cyano.

18. A method according to claim 17 wherein
$R^4$ is acetyl; or benzoyl nuclear substituted by 1 or 2 substituents selected from the group consisting of methyl, methoxy, fluoro, chloro, trifluoromethyl, nitro and cyano.

19. A method according to claim 12 wherein
R is alkyl of 1 to 3 carbon atoms;
$R^2$ is methyl or ethyl;
$R^3$ is phenyl substituted by 1 or 2 of the same or different substituents selected from the group consisting of alkyl of 1 or 2 carbon atoms, chloro, fluoro and trifluoromethyl; naphthyl; or tetramethylenephenyl; and R$^4$ is R$^5$CO wherein R$^5$ is alkyl of 1 to 4 carbon atoms, haloalkyl of 1 to 4 carbon atoms in the alkyl moiety and 1 to 3 halo atoms selected from the group consisting of chloro and fluoro; alkoxy of 1 to 4 carbon atoms; mono- or di-alkylamino of 1 to 4 carbon atoms in each alkyl moiety; or phenyl substituted by 1 to 3 substituents selected from the group consisting of alkyl of 1 or 4 carbon atoms, alkoxy of 1 or 4 carbon atoms, fluoro, chloro, and trifluoromethylsulphonyl.

20. A method according to claim 19 wherein
R$^4$ is R$^5$CO wherein R$^5$ is alkyl of 1 or 2 carbon atoms, haloalkyl of 1 or 2 carbon atoms in the alkyl moiety and 1 to 3 halo atoms selected from the group consisting of chloro and fluoro; alkoxy of 1 or 2 carbon atoms; mono- or di-alkylamino of 1 or 2 carbon atoms in each alkyl moiety; or phenyl substituted by 1 to 3 substituents selected from the group consisting of alkyl of 1 or 2 carbon atoms, alkoxy of 1 or 2 carbon atoms, fluoro, chloro and trifluoromethylsulphonyl.

21. A method according to claim 12 wherein
R is alkyl of 1 or 2 carbon atoms;
R$^2$ is methyl;
R$^3$ is dichlorophenyl or tetramethylenephenyl; and
R$^4$ is acetyl, methylbenzoyl, methoxybenzoyl, chlorobenzoyl, fluorobenzoyl or dichlorobenzoyl.

22. A method according to claim 12 wherein the compound is

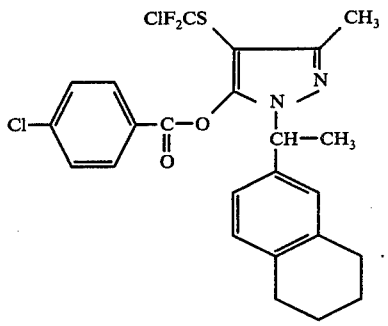

* * * * *